United States Patent
Asai et al.

(10) Patent No.: US 6,235,724 B1
(45) Date of Patent: May 22, 2001

(54) INJECTIONS CONTAINING LIPID A ANALOGUES AND PROCESS FOR THE PREPARATION THEREOF

(75) Inventors: Yasuyuki Asai; Katsumi Onai, both of Aichi; Kazuhide Ashizawa, Ibaraki; Kiyoshi Iwamoto; Yasuo Ishibashi, both of Gifu; Sumio Watanabe, Aichi, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/194,704

(22) PCT Filed: Jul. 3, 1997

(86) PCT No.: PCT/JP97/02316

§ 371 Date: Dec. 18, 1998

§ 102(e) Date: Dec. 18, 1998

(87) PCT Pub. No.: WO98/01139

PCT Pub. Date: Jan. 15, 1998

(30) Foreign Application Priority Data

Jul. 31, 1996 (JP) .................................................. 8-173615

(51) Int. Cl.⁷ ..................................................... A61K 31/70
(52) U.S. Cl. .............................. 514/53; 424/489; 514/951
(58) Field of Search .............................. 424/489; 514/53, 514/951

(56) References Cited

U.S. PATENT DOCUMENTS

| | | | |
|---|---|---|---|
| 4,942,167 | 7/1990 | Chiesi et al. | 514/226.5 |
| 5,530,113 * | 6/1996 | Christ et al. | 536/123.13 |
| 5,681,824 * | 10/1997 | Christ et al. | 514/54 |
| 5,750,664 * | 5/1998 | Christ et al. | 536/17.2 |
| 5,756,718 * | 5/1998 | Christ et al. | 536/123.13 |

FOREIGN PATENT DOCUMENTS

| | | |
|---|---|---|
| 1-299230 | 12/1989 | (JP) . |
| 4-198192 | 7/1992 | (JP) . |

OTHER PUBLICATIONS

R.B. Ramsey et al., Blood, 56, 307(1980).

J. Dijkstra et al., J. Immunol., 138, 2663(1987).

Haruhiko Takada and Shozo Kotani, Protein, Nucleic Acid and Enzyme, 31(4), 361(1986).

Yuji Ogawa et al., Metabolism 26(5), 415(1989).

Y.B. Kim et al., Eur. J. Biochem. 31, 230(1972).

* cited by examiner

*Primary Examiner*—Howard C. Lee
(74) *Attorney, Agent, or Firm*—Birch, Stewart, Kolasch & Birch, LLP

(57) ABSTRACT

The present invention provides a preparation for injection containing a lipid A analog and a process for preparing the same. A preparation for injection prepared by dissolving a lipid A analog or a pharmacologically acceptable salt thereof in an alkaline aqueous solution, at an elevated temperature if necessary, and then adding a buffer thereto, and a process for preparing the same.

24 Claims, No Drawings

INJECTIONS CONTAINING LIPID A ANALOGUES AND PROCESS FOR THE PREPARATION THEREOF

This application is the national phase under 35 U.S.C. §371 of prior PCT International Application No. PCT/JP97/02316 which has an International filing date of Jul. 3, 1997 which designated the United States of America.

BACKGROUND OF THE INVENTION

1. Field of the Invention

The present invention relates to a preparation for injection containing a lipid A analog or a pharmacologically acceptable salt thereof, and a process for preparing the same.

2. Prior Art

Lipid A, which is the main moiety causing activities of lipopolysaccharide (hereinafter referred to as LPS), has various biological activities such as macrophage stimulation, antitumor effect and pyrogenicity (for example, Haruhiko Takada and Shozo Kotani, *Protein, Nucleic Acid and Enzyme,* 31(4), 361(1986)).

Various lipid A analogs have recently been synthesized and examined for their biological activities (Yuji Ogawa et al., *Metabolism* 26(5), 415(1989)). Lipid A analogs originally have the glycolipid structure. Thus most of the lipid A analogs are sparingly soluble or insoluble in water, so that it is difficult to prepare an injection with lipid A analogs. Therefore, various investigations have been carried out in order to obtain a highly transparent aqueous solution thereof. As a result, it has been proposed, for example, to a dd triethylamine, bovine serum albumin, lipids, or the like as a solubilizing agent (Y. B. Kim, et al, *Eur. J. Biochem.* 31, 230(1972) and R. B. Ramsey, et al, *Blood,* 56, 307(1980), J. Dijkstra, et al, *J. Immunol.,* 138, 2663(1987)).

Furthermore, JP-A-4-198192 discloses a method employing basic amino acids or polyamines as a solubilizing agent. However, all of the pH of the aqueous solutions in the method are as high as around pH 10.

On the other hand, as a method of dispersing a lipid such as lecithin or the like in water to form aggregates of liposomes or the like, known is a method to add a lipid to a buffer having a pH around neutrality, followed by heating and sonication.

The method of solubilizing lipid A analogs using solubilizing agents is not satisfactory in view of the physical stability in water, chemical stability, pharmacological effects and safety, and hitherto has not been carried out on a practical basis. Moreover, a transparent solution of a lipid A analog could not be obtained also by the method of dispersing a lipid in a buffer having a pH around neutrality followed by sonication. Therefore, it has been eagerly desired to develop a practical injection containing a lipid A analog, that is, an injection which exhibits high transparency in the form of an aqueous solution, has pH ranging in values suitable for injection, and has excellent stability.

DISCLOSURE OF THE INVENTION

In order to overcome the above situation, the inventors of the present invention have intensively studied to find a highly transparent and stable preparation for injection containing a lipid A analog and a process for the preparation thereof. As a result, the present inventors discovered that the desired objects could be attained by the following embodiments. The present invention has been accomplished on the basis of this finding.

The present invention provides a preparation for injection prepared by dissolving a lipid A analog or a pharmacologically acceptable salt thereof in an alkaline aqueous solution and subsequently adding a buffer thereto.

The present invention also provides a process for preparing a preparation for injection, comprising dissolving a lipid A analog or a pharmacologically acceptable salt thereof in an alkaline aqueous solution and subsequently adding a buffer thereto.

Furthermore, the present invention provides a preparation for injection containing aggregates having an average particle diameter of 30 nm or less prepared by dissolving a lipid A analog or a pharmacologically acceptable salt thereof in an alkaline aqueous solution and subsequently adding a buffer thereto, and a process of the preparation thereof.

According to the present invention, it is possible to prepare a transparent and stable preparation for injection with a lipid A analog or a pharmacologically acceptable salt thereof (hereinafter referred to simply as a lipid A analog). This is therefore an object of the present invention.

Representative compounds of the lipid A analog of the present invention have a structure represented by the following chemical formula (I) or (II), and can be produced by the process disclosed in, for example, JP-A-5-194470 or WO96/39411.

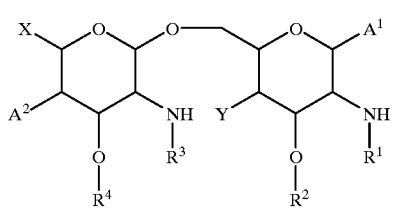

(I)

wherein at least one of $R^1$, $R^2$, $R^3$ and $R^4$ is

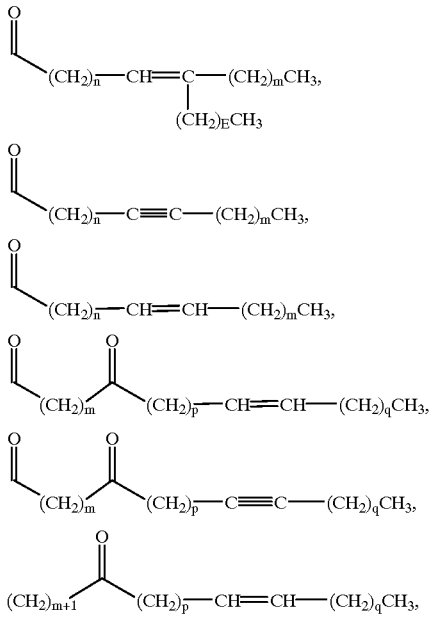

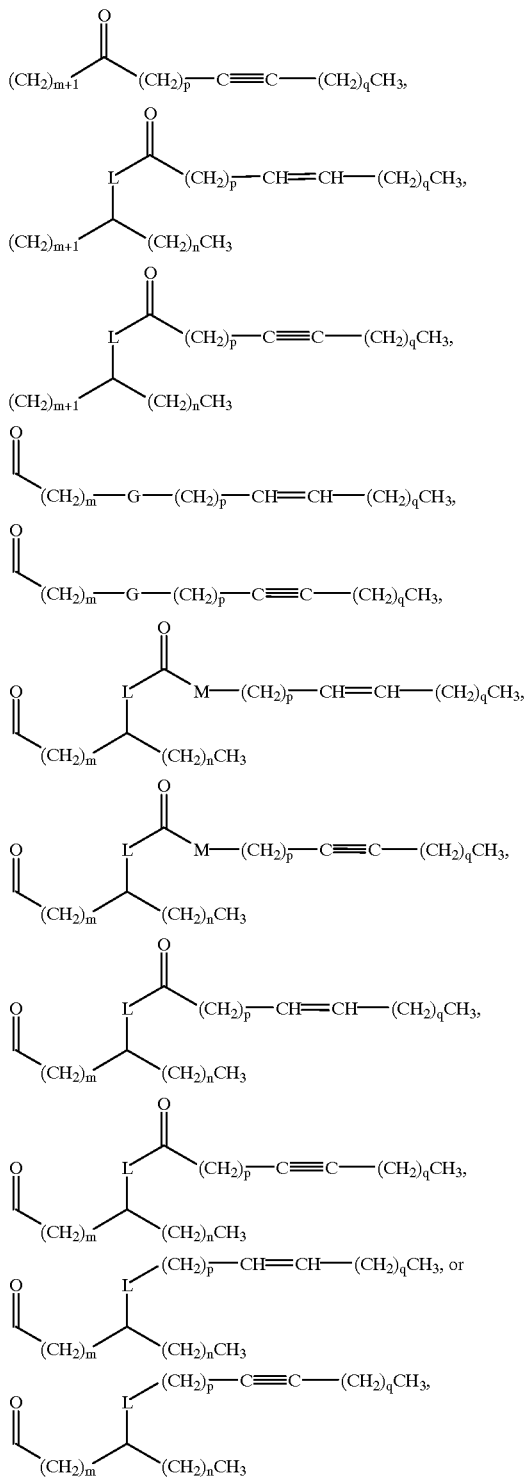

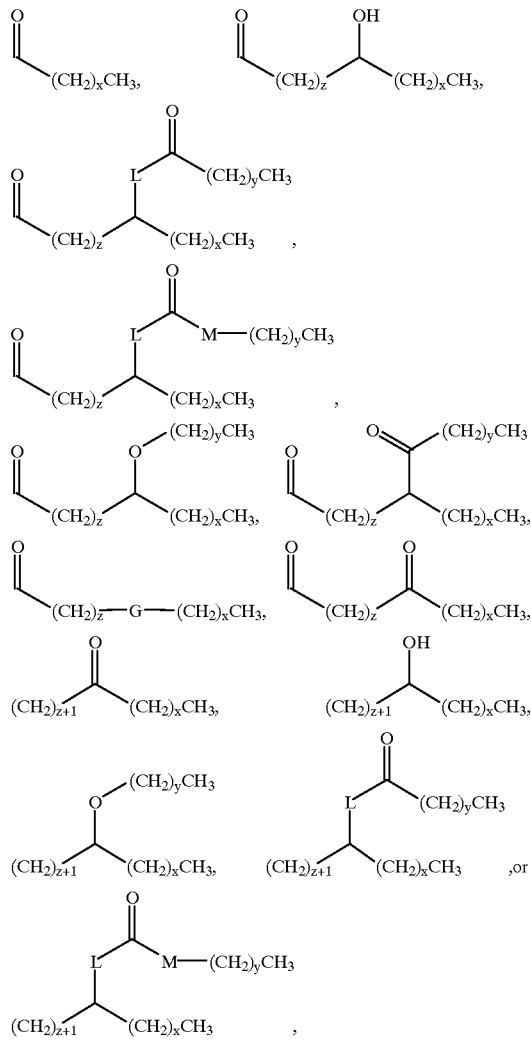

wherein each L is O, N or C; each M is O or N; each E independently is an integer of 0 to 14; each G independently is N, O, S, SO or $SO_2$; each m independently is an integer of 0 to 14; each n independently is an integer of 0 to 14; each p independently is an integer of 0 to 10; each q independently is an integer of 0 to 10, the rest of $R^1$, $R^2$, $R^3$ and $R^4$ are, independently of one another, wherein each L is O, N or C; each M is O or N; each x independently is an integer of 0 to 14; each y independently is an integer of 0 to 14; each z independently is an integer of 0 to 10; each G independently is N, O, S, SO or $SO_2$, $A^1$ and $A^2$ are, independently of one another, H, OH, $OCH_3$,

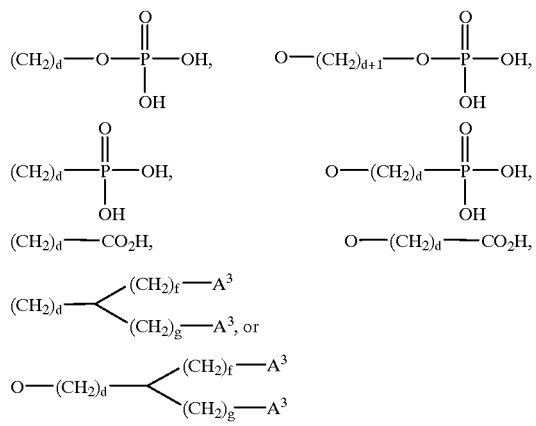

wherein each d independently is an integer of 0 to 5; each f independently is an integer of 0 to 5; each g independently is an integer of 0 to 5; each $A^3$ independently is

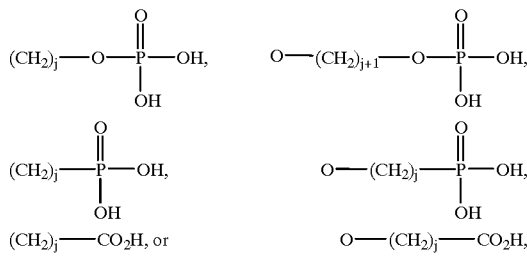

wherein each j independently is an integer of 0 to 14, X is H, $(CH_2)_tCH_3$, $(CH_2)_tOH$, $(CH_2)_tO(CH_2)_vCH_3$, $(CH_2)_tOPO(OH)_2$, $(CH_2)_t$—CH=CH—$(CH_2)_vCH_3$, $(CH_2)_t$—O—$R^5$,

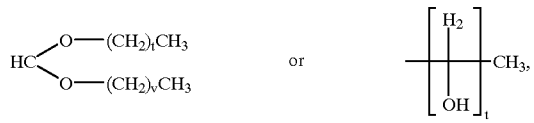

wherein t and v, are independently of one another, an integer of 0 to 14; $R^5$ is any of the above definitions of $R^1$ to $R^4$, Y is H, OH, $O(CH_2)_wCH_3$, a halogen atom,

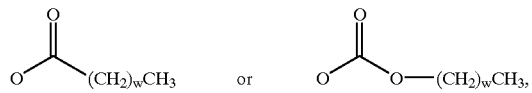

wherein w is an integer of 0 to 14.

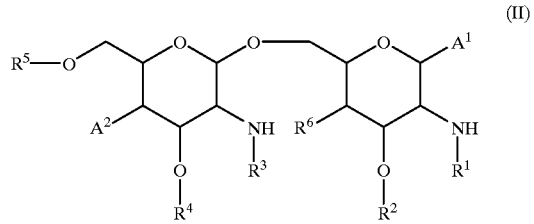

wherein $R^1$ is a group selected from the groups consisting of

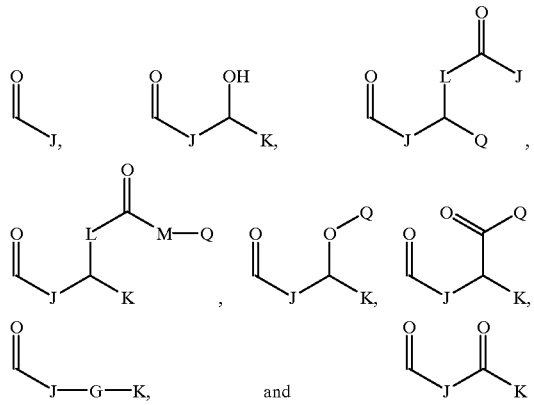

wherein J, K and Q are each a linear or branched alkyl group of 1 to 15 carbon atoms; L is O, $NH_2$ or $CH_2$; M is O or NH; G is NH, O, S, SO or $SO_2$, $R^2$ is a linear or branched alkyl group of 5 to 15 carbon atoms, $R^3$ is a group selected from the groups consisting of

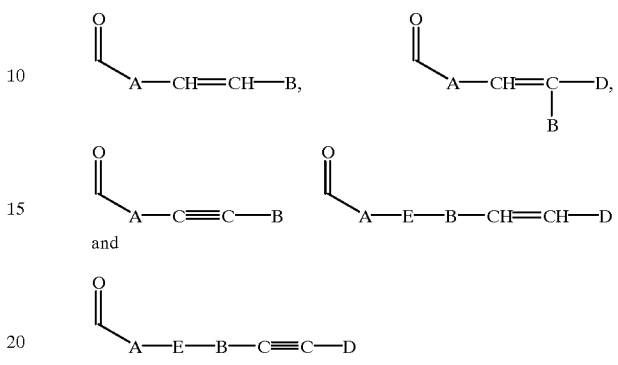

and wherein E is N, O, S, SO or $SO_2$; A, B and D are each a linear or branched alkyl group of 1 to 15 carbon atoms, $R^4$ is a group selected from the groups consisting of a linear or branched alkyl group of 4 to 20 carbon atoms and

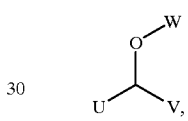

wherein U and V are each a linear or branched alkyl group of 2 to 15 carbon atoms; W is a hydrogen atom or a linear or branched alkyl group of 1 to 5 carbon atoms, $R^5$ is a group selected from the groups consisting of a hydrogen atom, J', —J'—OH, —J'—O—K', —J'—O—K'—OH and —J'—O—PO(OH)$_2$, wherein J' and K' are each a linear or branched alkyl group of 1 to 5 carbon atoms, $R^6$ is a group selected from the groups consisting of a hydroxyl group, a halogen atom, an alkoxy group of 1 to 5 carbon atoms, and an acyloxy group of 1 to 5 carbon atoms, $A^1$ and $A^2$ are, independently of one another, a group selected from the groups consisting of

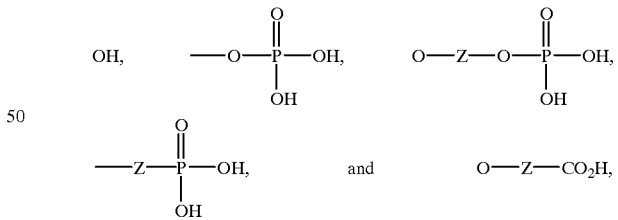

wherein Z is a linear or branched alkyl group of 1 to 10 carbon atoms.

Preferred examples of the lipid A analog for use in the present invention include 6-O-[2-deoxy-6-O-methyl-4-O-phosphono-3-O-[(R)-3-Z-dodec-5-enoyloxydecyl]-2-[3-oxo-tetradecanoylamido]-b-O-phosphono-a-D-glucopyranose]tetrasodium, a-D-glucopyranose, 3-O-decyl-2-deoxy-6-O-[2-deoxy-3-O-(3-methoxydecyl)-6-O-methyl-2-[(1-oxo-11-octadecenyl)amino]-4-O-phosphono-b-D-glucopyranosyl]-2-[(1,3-dioxotetradecyl)amino]-, 1-(dihydrogenphosphate), disodium[6(2Z, 3R)]; and a-D-glucopyranose, 3-O-decyl-2-deoxy-6-O-[2-deoxy-3-O-(3- methoxydecyl)-6-O-methyl-2-[(1-oxo-11-octadecenyl) amino]-4-O-phosphono-b-D-glucopyranosyl]-2-[(1,3-dioxotetradecyl)amino]-, 1-(dihydrogenphosphate), tetrasodium[6(2Z, 3R)]. These compounds are represented by the following chemical structural formulae (III) and (IV).

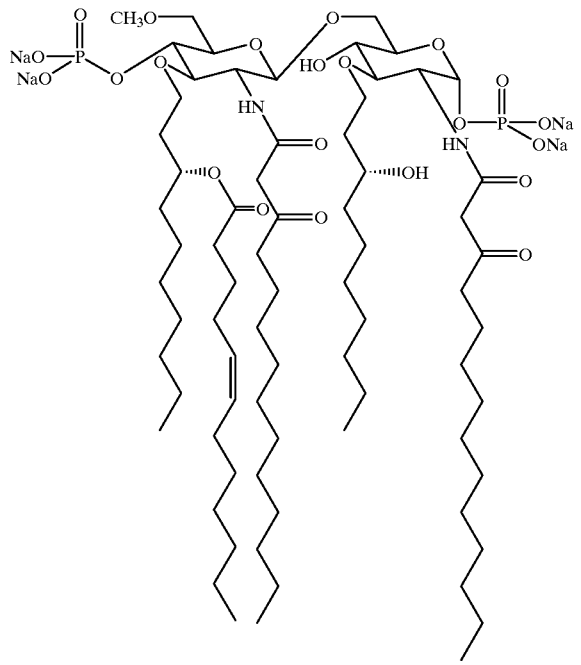

(III)

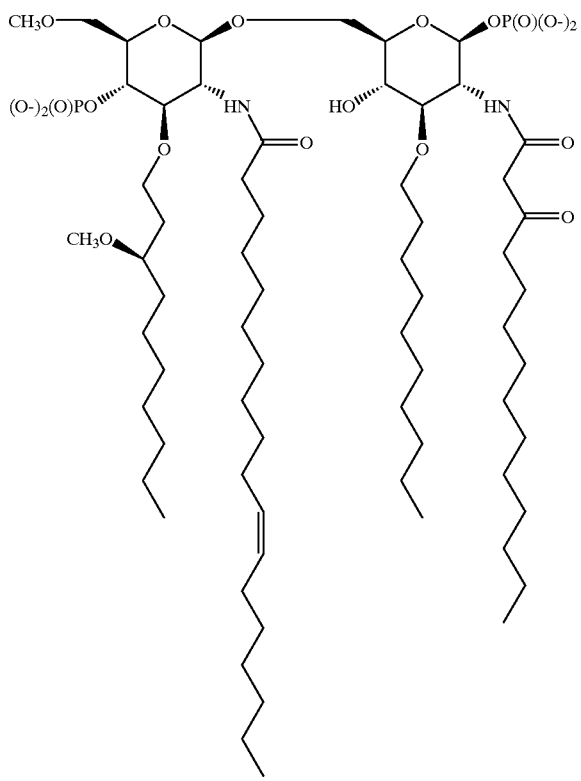

(IV)

The alkaline aqueous solution for use in the present invention may be an aqueous solution of the hydroxide of an alkali metal such as sodium hydroxide, potassium hydroxide or the like. However, an aqueous solution of sodium hydroxide is preferred. The concentration of the aqueous solution generally ranges from 0.0001 M to 0.1 M, preferably from 0.0005 M to 0.01 M, and more preferably from 0.001 M to 0.005 M.

In the present invention, after an alkaline aqueous solution is added to a lipid A analog, the temperature of the mixture may be elevated. The elevated temperature must be higher than the phase transition temperature of the lipid A analog or a pharmacologically acceptable salt thereof, but has no more limitation. The elevated temperature generally ranges from 30° C. to 60° C., preferably 45° C. to 55° C. The stirring time while elevating the temperature generally ranges from 10 minutes to 3 hours. Stirring may be carried out with a conventional apparatus. The stirring time necessary to obtain a transparent solution (having a turbidity of 0.6 NTU or lower) varies depending on lipid A analogs used. For the compound represented by the above formula (III), the stirring time generally requires 90 minutes or longer at an elevated temperature of 40° C. or lower,-or may be within 60 minutes at an elevated temperature of 4° C. or higher. When a lipid A analog is dissolved in a heated alkaline aqueous solution, a lipid A analog may be added to an alkaline aqueous solution which is heated in advance. Alternatively, after a lipid A analog is added to an alkaline aqueous solution, the mixture may be heated. In the present invention, the purpose of elevating the temperature is to accelerate hydration of lipid A analogs to improve dispersibility by elevating the temperature to the phase transition temperature of lipid A analogs or higher, to thereby obtain a transparent solution by stirring for a shortened period of time.

Examples of the component of the buffer for use in the present invention include phosphates, Tris(hydroxymethyl)aminomethane, citrates, glycine and the like. The concentration of the buffer generally ranges from 1 mM to 20 mM. The final pH value of the aqueous solution of the lipid A analog is preferably 4 to 9, more preferably 6 to 8, still more preferably 6.8 to 7.8. The final pH value may be adjusted by adding a solution of sodium hydroxide, hydrochloric acid, or the like after the addition of the buffer.

If necessary, addition of saccharides and/or amino acids to the buffer may give a more preferable result. In this case, saccharides and/or amino acids to be added may be either one, or two or more kinds thereof. Examples of the saccharide include milk sugar (lactose), sorbitol, glucose, trehalose, mannitol, dextran, and the like. Examples of the amino acid include neutral amino acids such as glycine, acidic amino acids such as aspartic acid, and basic amino acids such as arginine.

In the present invention, the resulting lipid A analog aqueous solution may be freeze-dried by a conventional method to obtain a freeze-dried preparation. Namely, lipid A or an analog thereof is dissolved in an alkaline aqueous solution, further stirred at an elevated temperature if necessary, followed by addition of a buffer to adjust pH of the mixture. After sterilizing filtration, the mixture is filled into a vial or the like, followed by freezing and drying to give a freeze-dried preparation.

When a preparation for injection according to the present invention is administered in the form of aqueous solution, the osmotic pressure ratio of the preparation is preferably adjusted to a value suitable for administrating to humans, generally around 1.

In the preparation for injection according to the present invention, molecules of the lipid A analog aggregates to form particles which are roughly spherical in shape and have an average particle diameter of about 30 nm or smaller. The aggregates do not change in size between immediately after the production of the preparation for injection and after reconstitution of a freeze-dried preparation. Generally speaking, freeze-drying often destroys aggregates. However, in the present invention, the particle diameter of the aggregates still remains 30 nm or smaller even after reconstitution. This is one of the prominent effects of the present invention. According to a detailed study, the aggregates in the present invention, in the case of the compound represented by the above formula (III), have an inner aqueous phase of about 0.196 liter per mole (at pH 11.0). Continuous stirring in preparation produces aggregates having an almost constant diameter of about 15 nm. Therefore, the particle diameter of the aggregates in the present invention ranges from about 15 nm to 30 nm, in the case of the general production process.

The aggregates of the lipid A analog in the present invention are hardly influenced by coexisting magnesium ion or calcium ion on particle diameter, turbidity and the like. On the other hand, magnesium ion or calcium ion influences the aggregates on membrane fluidity. Thus, membrane fluidity of the aggregates lowers if these metal ions are present. Membrane fluidity affects the pharmacokinetics after the administration of lipid A analogs. Decrease in membrane fluidity accelerates the loss of lipid A analogs from living matter.

EXAMPLES

The present invention is explained below in more detail by reference to the following examples, but the present invention should not be construed as being limited thereto.

Example 1

To 90 ml of a 0.003 M solution of sodium hydroxide of 45° C., 60 mg of the lipid A analog represented by the above formula (III) was added and dissolved therein, and stirred for 30 minutes at the same temperature. This mixture was taken out in an amount of 5 ml, and the turbidity thereof was evaluated with a turbidimeter. The turbidity of the solution was 0.178 NTU. To 7.5 ml of this alkaline aqueous solution, 30 ml of a 7.08 mM phosphate buffer containing 16.7% of lactose was added. Then, the pH of the solution was adjusted to pH 7.39 with a 0.3% solution of sodium hydroxide, followed by the addition of distilled water for injection to make the total volume of the resulting solution 50 ml. The turbidity of this aqueous solution was 0.181 NTU. To a vial, 5.3 ml of this aqueous solution was placed, and freeze-dried with a vacuum freeze-drying apparatus (Triomaster A04, Kyowa Manufacturing Co., Ltd.).

Example 2

To 90 ml of a 0.003 M solution of sodium hydroxide of 55° C., 60 mg of the lipid A analog used in Example 1 was added and dissolved therein, and stirred for 60 minutes at the same temperature. This alkaline aqueous solution was taken out in an amount of 5 ml, and the turbidity thereof was evaluated with a turbidimeter. The turbidity of the solution was 0.133 NTU. To 7.5 ml of this alkaline aqueous solution, 30 ml of a 7.08 mM phosphate buffer containing 16.5% of lactose was added. Then, the pH of the solution was adjusted to pH 7.41 with a 0.3% aqueous solution of sodium hydroxide, followed by the addition of distilled water for injection to make the total volume of the resulting solution 50 ml. The turbidity of this aqueous solution was 0.212 NTU.

Example 3

To 90 ml of a 0.001 M solution of sodium hydroxide of 50° C., 60 mg of the lipid A analog used in Example 1 was added and dissolved therein, and stirred for 60 minutes at the same temperature. This alkaline aqueous solution was taken out in an amount of 5 ml, and the turbidity thereof was evaluated with a turbidimeter. The turbidity of the solution was 0.142 NTU. To 7.5 ml of this alkaline aqueous solution, 30 ml of a 7.08 mM buffer of Tris (hydroxymethyl) aminomethane containing 8.35% of mannitol was added. Then, the pH of the solution was adjusted to pH 7.39 with a 1 N hydrochloric acid, followed by the addition of distilled water for injection to make the total volume of the resulting solution 50 ml. The turbidity of this aqueous solution was 0.133 NTU.

Example 4

To 90 ml of a 0.005 M solution of sodium hydroxide of 50.C, 60 mg of the lipid A analog used in Example 1 was added to dissolved therein, and stirred for 60 minutes at the same temperature. This alkaline aqueous solution was taken out in an amount of 5 ml, and the turbidity thereof was evaluated with a turbidimeter. The turbidity of the solution was 0.150 NTU. To 7.5 ml of this alkaline aqueous solution, 30 ml of a 7.08 mM phosphate buffer containing 16.5% of lactose was added. Then, the pH of the solution was adjusted to pH 7.37 with a 0.3% aqueous solution of sodium hydroxide, followed by the addition of distilled water for injection to make the total volume of the resulting solution 50 ml. The turbidity of this aqueous solution was 0.205 NTU.

Example 5

To 90 ml of a 0.003 M solution of sodium hydroxide of 35° C., 60 mg of the lipid A analog used in Example 1 was added and dissolved therein, and stirred for 150 minutes at the same temperature. This alkaline aqueous solution was taken out in an amount of 5 ml, and the turbidity thereof was evaluated with a turbidimeter. The turbidity of the solution was 0.669 NTU. To 7.5 ml of this alkaline aqueous solution, 30 ml of a 7.08 mM phosphate buffer containing 8.35% of dextran 70 (average molecular weight of 70,000) was added. Then, the pH of the solution was adjusted to pH 7.30 with a 0.3% aqueous solution of sodium hydroxide, followed by the addition of distilled water for injection to make the total volume of resulting solution 50 ml. The turbidity of this aqueous solution was 1.25 NTU.

Example 6

To 9.0 ml of a 0.01 M solution of sodium hydroxide, 6.09 mg of the lipid A analog represented by the above formula (IV) was added, and stirred for 60 minutes. This solution had a pH of 12.08. To this solution, 30 ml of a phosphate buffer containing lactose was added. The resulting solution had a pH of 7.46. Distilled water for injection was added to this solution to make the total volume of the resulting solution 60 ml. This solution was an injection solution of pH 7.50 containing the lipid A analog in a concentration of 0.1 mg/ml, 10% of lactose, and a 4.25 mM phosphate buffer.

Example 7

After the injection solution obtained in Example 6 was subjected to sterilizing filtration, the injection solution was poured into vials in an amount of 3 ml, respectively, and freeze-dried to give freeze-dried preparations containing a lipid A analog. The conditions of the freeze-drying were as follows (freeze-drying apparatus: EDWARD Model Lyo fast S08):

Freezing temperature: −40° C.; primary drying temperature: 20° C.; primary drying pressure: 0.075±0.025 mbar; secondary drying temperature: 27° C.; secondary drying pressure: (the maximum capability of the apparatus); secondary drying time: 18 hours.

Example 8

To 9.0 ml of a 0.003 M solution of sodium hydroxide, 40.16 mg of the lipid A analog used in Example 6 was added, and stirred for 60 minutes. This solution had a pH of 11.49. To this solution, 10 ml of a phosphate buffer containing lactose was added. The resulting solution had a pH of 8.44. Then, the pH of the solution was adjusted to pH 7.4 with a 4% of phosphoric acid, followed by the addition of distilled water for injection to make the total volume of the resulting solution 20 ml. This solution was an injection solution of pH 7.51 containing the lipid A analog in a concentration of 2.0 mg/ml, 10% of lactose, and a 4.25 mM phosphate buffer.

Example 9

After the injection solution obtained in Example 8 was subjected to sterilizing filtration, the injection solution was poured into vials in an amount of 3 ml, respectively, and freeze-dried to give freeze-dried preparations containing a lipid A analog. The conditions of the freeze-drying were as follows (freeze-drying apparatus: EDWARD Model Lyo fast S08):

Freezing temperature: −40° C.; primary drying temperature: 20° C.; primary drying pressure: 0.075±0.025 mbar; secondary drying temperature: 27° C.; secondary drying pressure: (the maximum capability of the apparatus); secondary drying time: 18 hours.

Experimental examples are given below to demonstrate the effects according to the present invention.

Experimental Example 1

Evaluation of transparency of a preparation according to the present invention

1. Experimental Methods

The aqueous solutions of a lipid A analog prepared in the following Comparative Example and the Present Method 1 was examined for turbidity. The measurement was carried out with a Hach 2100AN Turbidimeter.

Comparative Example

To a 4.25 mM phosphate buffer containing 10% of lactose of 50° C., 60 mg of the lipid A analog used in Example 1 was added and dissolved therein, and stirred at the same temperature. A 12.5 ml sample was collected after 30 minutes, 60 minutes, 120 minutes, and 180 minutes of stirring, respectively. The samples were examined for turbidity using 5 ml of the respective samples. Furthermore, a 4.25 mM phosphate buffer containing 10% of lactose was added to 7.5 ml of each sample solution to make the total volume of the resulting solution 50 ml. The resulting solutions were examined for turbidity and pH.

Present Method 1

To 90 ml of a 0.003 M aqueous solution of sodium hydroxide of 50° C., 60 mg of the lipid A analog used in Example 1 was added and dissolved therein, and stirred at the same temperature. A 12.5 ml sample of the alkaline aqueous solution was collected after 30 minutes, 60 minutes, 120 minutes, and 180 minutes of stirring, respectively. The samples were examined for turbidity with a turbidimeter using 5 ml of the respective samples. Furthermore, 30 ml of a 7.08 mM phosphate buffer containing 16.5% of lactose was added to 7.5 ml of each sample of the alkaline aqueous solution. Then, the pH of the respective solution was adjusted to about pH 7.4 with a 0.3% aqueous solution of sodium hydroxide. Thereafter, distilled water for injection was added thereto to make the total volume of the resulting solution 50 ml. The resulting solutions were examined for turbidity and pH.

2. Experimental Results

The results obtained by the above Experimental methods are shown in Table 1.

TABLE 1

|  | Stirring Time | Turbidity (NTU) Alkaline solution | Turbidity (NTU) After addition of a buffer | PH After addition of a buffer |
| --- | --- | --- | --- | --- |
| Comparative Example | 30 min | 39.6 | 14.4 | 7.38 |
|  | 60 min | 45.7 | 15.0 | 7.36 |
|  | 120 min | 44.6 | 13.5 | 7.36 |
|  | 180 min | 47.5 | 13.4 | 7.37 |
| Present Method 1 | 30 min | 0.163 | 0.188 | 7.40 |
|  | 60 min | 0.154 | 0.194 | 7.37 |
|  | 120 min | 0.151 | 0.204 | 7.36 |
|  | 180 min | 0.152 | 0.181 | 7.39 |

The results shown in Table 1 clearly demonstrate that the aqueous solution of the lipid A analog obtained in Present Method 1 according to the present invention exhibits excellent transparency superior to the aqueous solution of the lipid A analog prepared in Comparative Example which is a representative conventional method.

Experimental Example 2

Evaluation of reconstitution property of a freeze-dried preparation of a lipid A analog.

1. Experimental Methods

Present Method 2

To 90 ml of a 0.003 M aqueous solution of sodium hydroxide of 50° C., 60 mg of the lipid A analog used in Example 1 was added and dissolved therein, and stirred at the same temperature. A 12.5 ml sample of the alkaline aqueous solution was collected after 30 minutes, 60 minutes, 120 minutes, and 180 minutes of stirring, respectively. The samples were examined for turbidity with a turbidimeter using 5 ml of the respective samples. Furthermore, 30 ml of a 7.08 mM phosphate buffer containing 16.5% of lactose was added to 7.5 ml of each sample of the alkaline aqueous solution. Then, the pH of the respective solutions was adjusted to about pH 7.4 with a 0.3% aqueous solution of sodium hydroxide. Thereafter, distilled water for injection was added thereto to make the total volume of the resulting solution 50 ml. 5.3 ml of this aqueous solution was placed in a vial, and freeze-dried using a vacuum freeze-drying apparatus—(Kyowa Manufacturing Co., Ltd., Triomaster A-04). Furthermore, 5 ml of distilled water for injection was added to the resulting freeze-dried preparation to dissolve the preparation therein again. The resulting solution was examined for turbidity using a Hach 2100AN Turbidimeter.

Present Method 3

To 100 ml of a 0.003 M aqueous solution of sodium hydroxide of 50° C., 200 mg of the lipid A analog used in Example 1 was added and dissolved therein, and stirred at the same temperature. A 7.5 ml sample of the alkaline aqueous solution was collected after 30 minutes, 60 minutes, 120 minutes, and 180 minutes of stirring, respectively. The samples were examined for turbidity with a turbidimeter using 5 ml of the respective samples. Furthermore, 30 ml of a 7.08 mM phosphate buffer containing 16.5% of lactose was added to 2.5 ml of each sample of the alkaline aqueous solution. Then, the pH of the respective solutions was adjusted to about pH 7.4 with a 0.3% aqueous solution of sodium hydroxide. Thereafter, distilled water for injection was added thereto to make the total volume of the resulting solution 50 ml. 5.3 ml of this aqueous solution was placed in a vial, and freeze-dried using a vacuum freeze-drying apparatus (Kyowa Manufacturing Co., Ltd., Triomaster A-04). Furthermore, 5 ml of distilled water for injection was added to the resulting freeze-dried preparation to dissolve the preparation therein again. The resulting solution was examined for turbidity. The measurement of turbidity was carried out using a Hach 2100AN Turbidimeter.

The results are shown in Table 2.

TABLE 2

| | Stirring Time | Turbidity (NTU) aqueous solution before freeze-drying | Turbidity (NTU) Rehydrated Solution after freeze-drying |
|---|---|---|---|
| Present Method 2 | 30 min | 0.183 | 0.217 |
| | 60 min | 0.182 | 0.211 |
| | 120 min | 0.141 | 0.206 |
| | 180 min | 0.157 | 0.193 |
| Present Method 3 | 30 min | 0.149 | 0.219 |
| | 60 min | 0.167 | 0.190 |
| | 120 min | 0.172 | 0.178 |
| | 180 min | 0.152 | 0.200 |

The results shown in table 2 clearly demonstrate that the freeze-dried preparations according to the present invention exhibits excellent transparency even when they are dissolved in water again.

What is claimed is:

1. A preparation for injection prepared by dissolving a lipid A analog or a pharmacologically acceptable salt thereof in an alkaline aqueous solution and subsequently adding a buffer thereto, wherein the alkaline aqueous solution containing the lipid A analog is heated for 10 minutes to 3 hours at a temperature range of 30 to 60° C. before adding the buffer thereto.

2. The preparation according to claim 1 wherein the concentration of base in the alkaline aqueous solution is in the range of 0.0001M to 0.1M.

3. The preparation for injection as claimed in claim 1, wherein the lipid A analog or a pharmacologically acceptable salt thereof is a compound represented by the following formula (I) or a pharmacologically acceptable salt thereof:

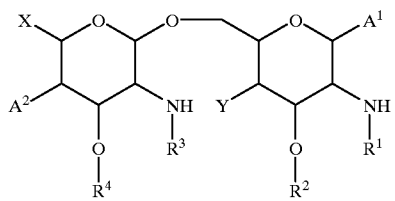

(I)

wherein at least one of $R^1$, $R^2_1$ $R^3$ and $R^4$ is

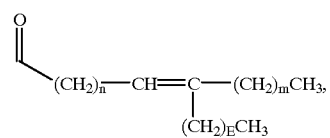

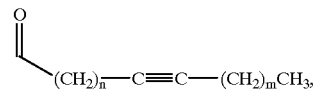

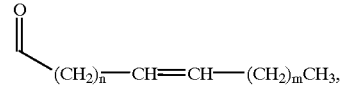

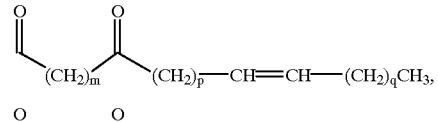

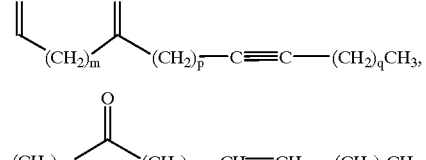

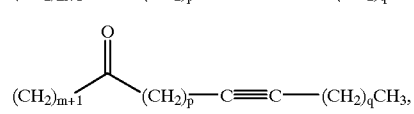

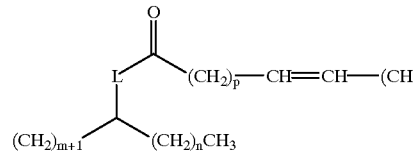

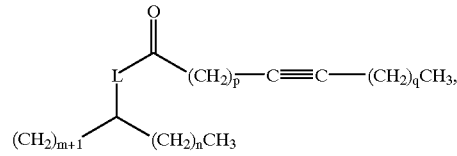

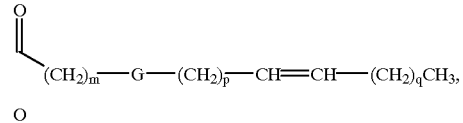

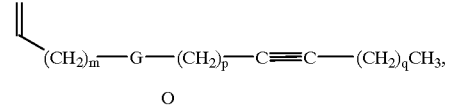

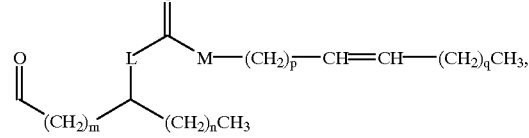

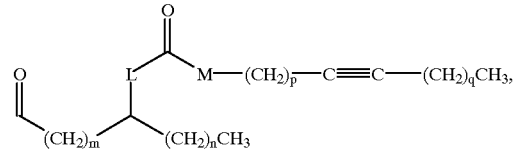

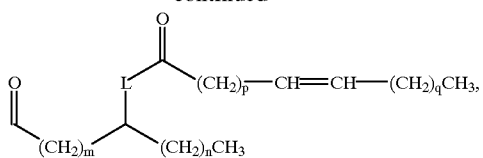
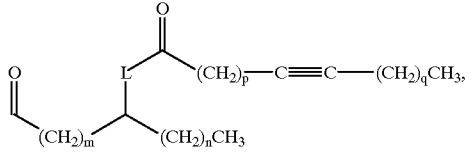
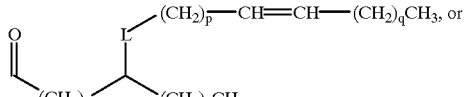
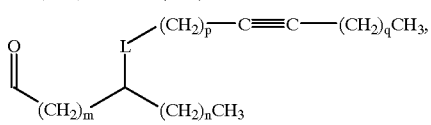

wherein each L is O, N or C; each M is O or N; each E independently is an integer of 0 to 14; each G independently is N, O, S, SO or $SO_2$; each m independently is an integer of 0 to 14; each n independently is an integer of 0 to 14; each p independently is an integer of 0 to 10; each q independently is an integer of 0 to 10, the rest of $R^1$, $R^2$, $R^3$ and $R^4$ are, independently of one another,

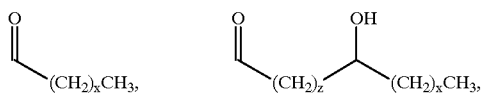
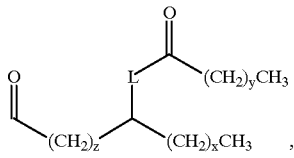
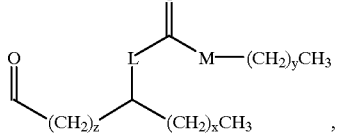
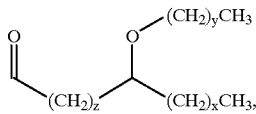
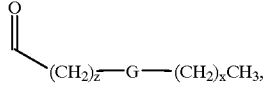
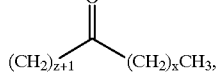
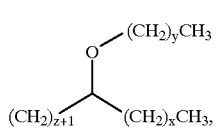
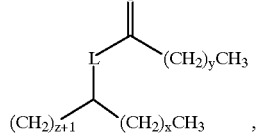

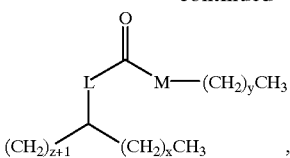

wherein each L is O, N or C; each M is O or N; each x independently is an integer of 0 to 14; each y independently is an integer of 0 to 14; each z independently is an integer of 0 to 10; each G independently is N, O, S, SO or $SO_2$, $A^1$ and $A^2$ are, independently of one another, H, OH, $OCH_3$,

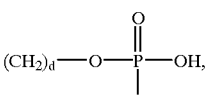
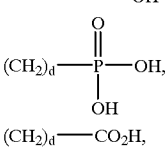
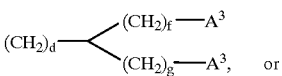
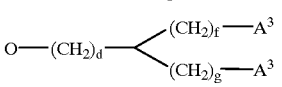

wherein each d independently is an integer of 0 to 5; each f independently is an integer of 0 to 5; each g independently is an integer of 0 to 5; each $A^3$ independently is

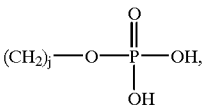
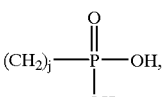
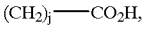

wherein each j independently is an integer of 0 to 14; X is H, $(CH_2)_tCH_3$, $(CH_2)_tOH$, $(CH_2)_tO(CH_2)_vCH_3$, $(CH_2)_tOPO(OH)_2$, $(CH_2)_t$—CH=CH—$(CH_2)_vCH_3$, $(CH_2)_t$—O—$R^5$,

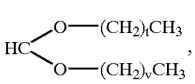
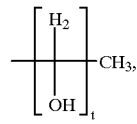

wherein t and v are, independently of one another, an integer of 0 to 14; $R^5$ is any of the above definitions of $R^1$ to $R^4$, Y is H, OH, O(CH$_2$)$_w$CH$_3$, a halogen atom,

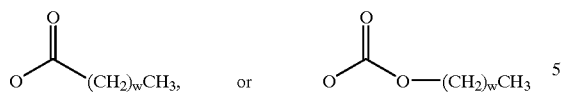

wherein w is an integer of 0 to 14.

4. The preparation for injection as claimed in claim 1, wherein the lipid A analog or a pharmacologically acceptable salt thereof is a compound represented by the following formula (II) or a pharmacologically acceptable salt thereof:

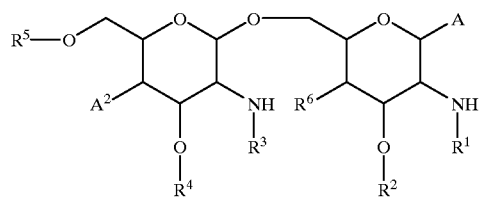 (II)

wherein R$^1$ is a group selected from the groups consisting of

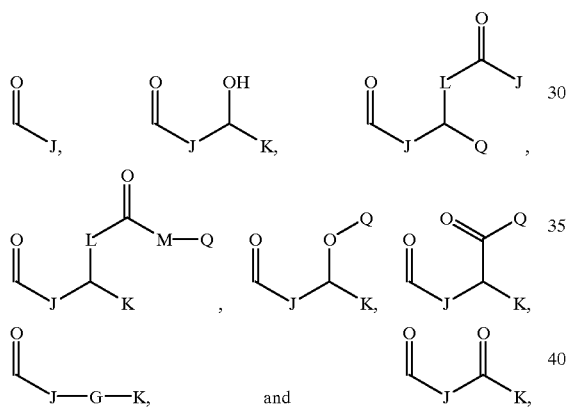

wherein J, K and Q are each a linear or branched alkyl group of 1 to 15 carbon atoms; L is O, NH$_2$ or CH$_2$; M is O or NH; G is NH, O, S, SO or SO$_2$, R$^2$ is a linear or branched alkyl group of 5 to 15 carbon atoms, R$^3$ is a group selected from the groups consisting of

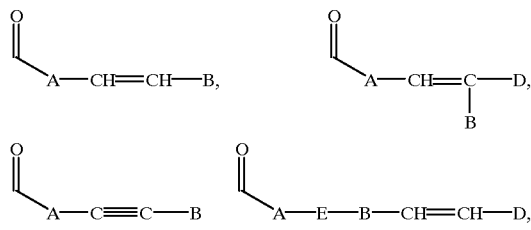

and

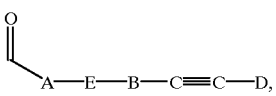

wherein E is N, O, S, SO or SO$_2$; A, B and D are each a linear or branched alkyl group of 1 to 15 carbon atoms, R$^4$ is a group selected from the groups consisting of a ear or branched alkyl group of 4 to 20 carbon atoms and

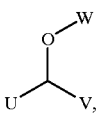

wherein U and V are each a linear or branched alkyl group of 2 to 15 carbon atoms; W is a hydrogen atom or a linear or branched alkyl group of 1 to 5 carbon atoms, R$^5$ is a group selected from the groups consisting of a hydrogen atom, J', —J'—OH, —J'—O—K', —J'—O—K'—OH and —J'—O—PO(OH)$_2$, wherein J' and K' are each a linear or branched alkyl group of 1 to 5 carbon atoms, R$^6$ is a group selected from the groups consisting of a hydroxyl group, a halogen atom, an alkoxy group of 1 to 5 carbon atoms, and an acyloxy group of 1 to 5 carbon atoms, A$^1$ and A$^2$ independently are each a group selected from the groups consisting of

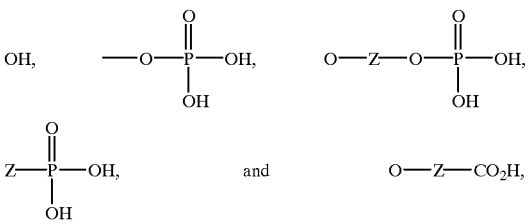

wherein Z is a linear or branched alkyl group of 1 to 10 carbon atoms.

5. The preparation for the injection as claimed in claim 1, wherein the preparation for the injection is an aqueous injection.

6. The preparation for the injection as claimed in claim 1, wherein the preparation for the injection is a freeze-dried preparation.

7. The preparation for injection as claimed in claim 1, wherein the buffer has a pH of 4 to 9.

8. The preparation for injection as claimed in claim 1, wherein the buffer has a pH of 4 to 9 and containing a saccharide.

9. The preparation for injection according to claim 1 prepared by dissolving the lipid A analog represented by formula (III) in the alkaline aqueous solution (III)

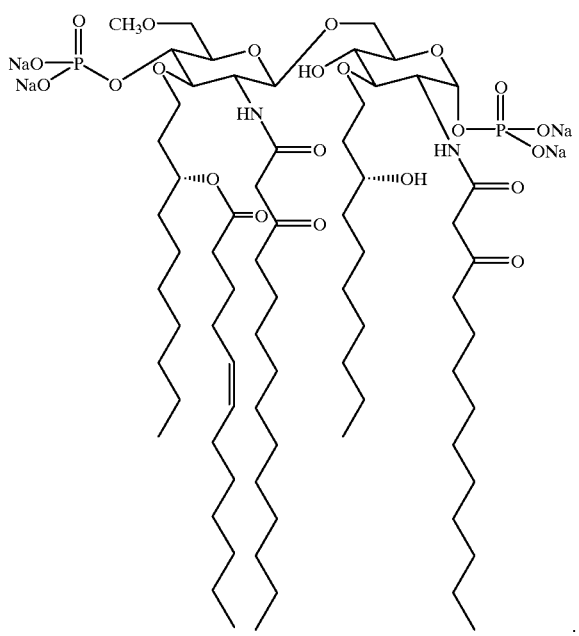

10. The preparation for injection according to claim 1 prepared by dissolving the lipid A analog represented by the formula (IV) in the alkaline aqueous solution (IV)

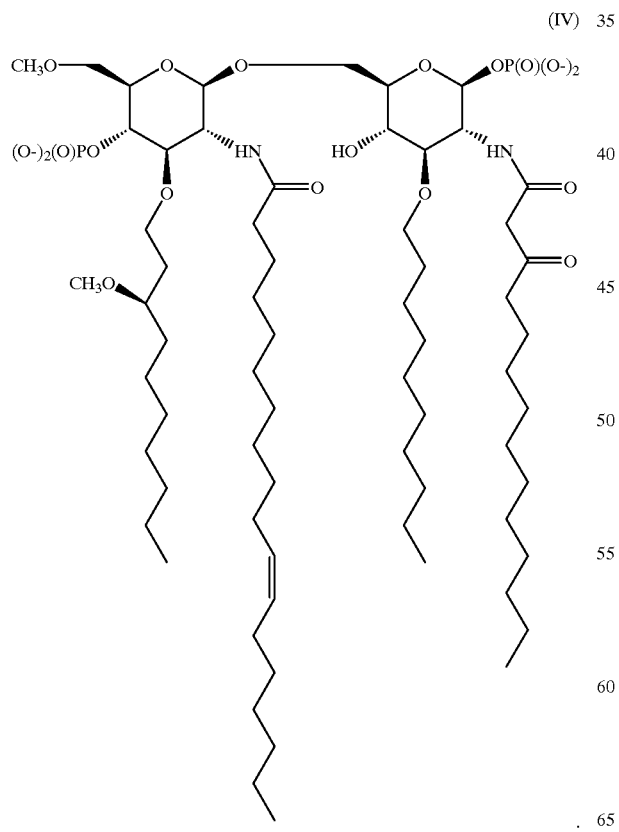

11. The preparation for injection according to claim 1, which contains aggregates having an average particle diameter of 30 nm or smaller.

12. The preparation according to claim 9, wherein the concentration of base in the alkaline aqueous solution is in the range of 0.0001M to 0.1M.

13. The preparation according to claim 10, wherein the concentration of base in the alkaline aqueous solution is in the range of 0.0001M to 0.1M.

14. The preparation according to claim 13, wherein the concentration of base in the alkaline aqueous solution is in the range of 0.0001M to 0.1M.

15. A process for preparing a preparation for injection comprising:

dissolving a lipid A analog or a pharmacologically acceptable salt thereof in an alkaline aqueous solution by heating the alkaline aqueous solution containing the lipid A analog at a temperature of 30 to 60° C. for 10 minutes to 3 hours, and subsequently adding a buffer thereto.

16. The process for preparing a preparation for injection as claimed in claim 15, wherein the buffer has a pH of 4 to 9.

17. The process according to claim 15, wherein the concentration of base in the alkaline aqueous solution is in the range of 0.0001M to 0.1M.

18. The process according to claim 15, wherein the lipid A analog or a pharmacologically acceptable salt thereof is a compound represented by the following formula (I) or a pharmacologically acceptable salt thereof:

(I)

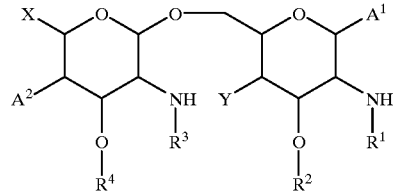

wherein at least one $R^1$, $R^2$, $R^3$ and $R^4$ is

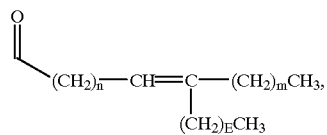

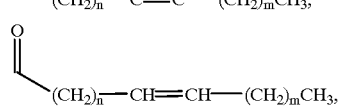

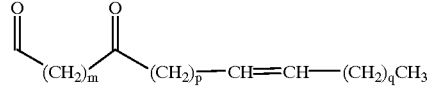

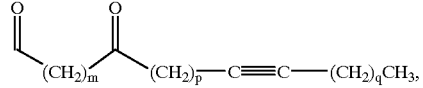

21
-continued

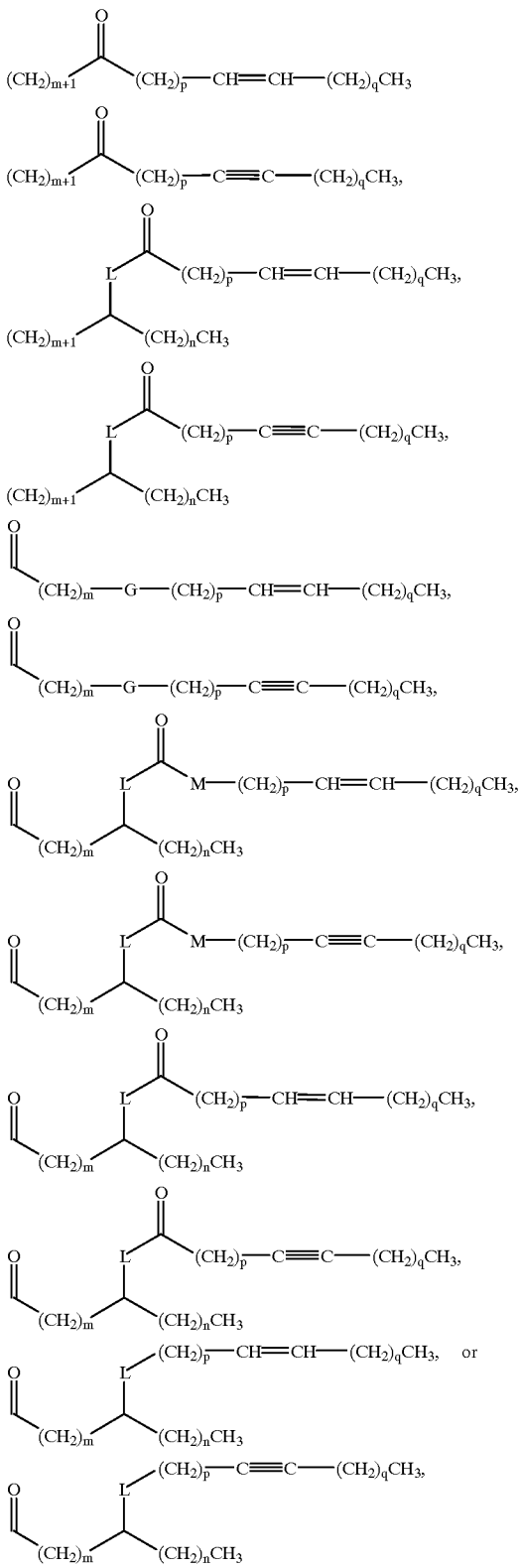

wherein each L is O, N, or C; each M is O or N; each E independently is an integer of 0 to 14; each G independently is N, O, S, SO or SO$_2$; each m independently is an integer of 0 to 14; each n independently is an integer of 0 to 10; each q independently is an integer of 0 to 10, the rest of R$^1$, R$^2$,

22

R$^3$ and R$^4$ are, independently of one another,

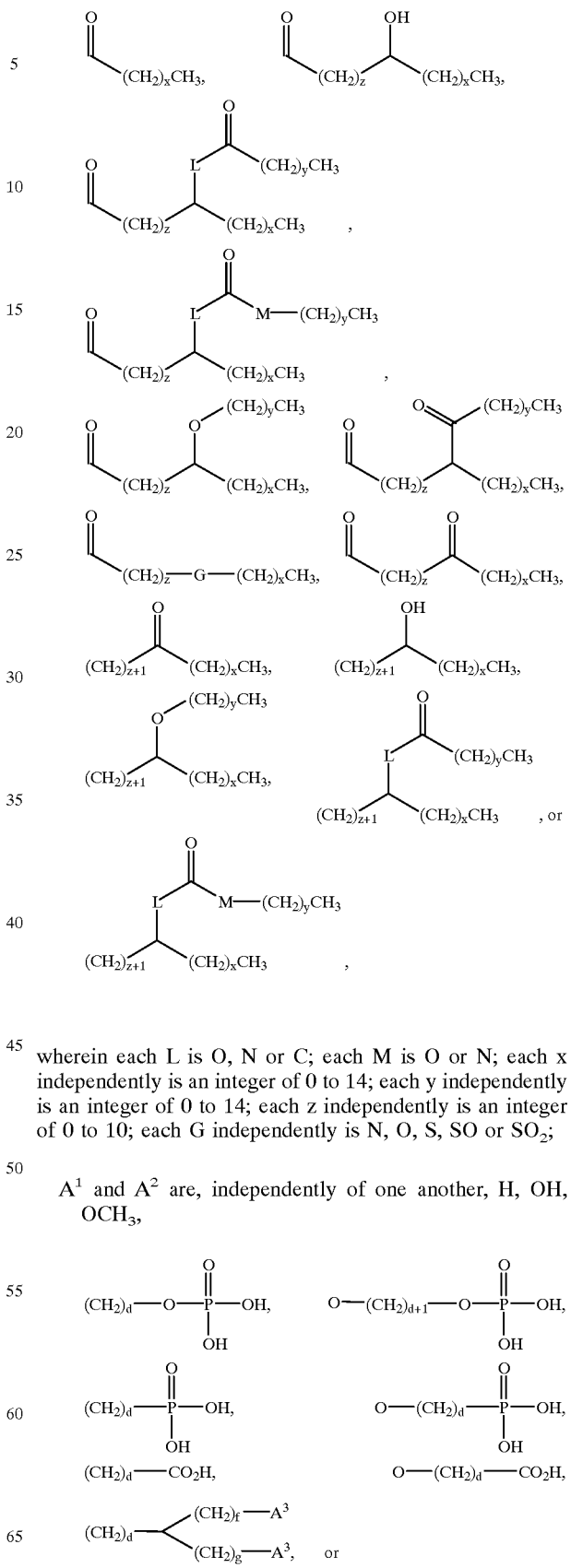

wherein each L is O, N or C; each M is O or N; each x independently is an integer of 0 to 14; each y independently is an integer of 0 to 14; each z independently is an integer of 0 to 10; each G independently is N, O, S, SO or SO$_2$;

A$^1$ and A$^2$ are, independently of one another, H, OH, OCH$_3$,

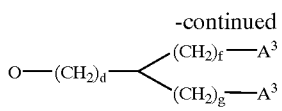

wherein each d independently is an integer of 0 to 5; each f independently is an integer of 0 to 5; each g independently is an integer of 0 to 5; each $A^3$ independently is

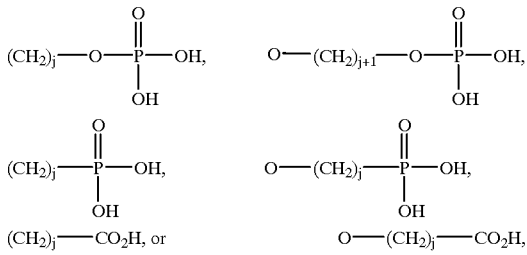

wherein each j independently is an integer of o to 14; X is H, $(CH_2)_tCH_3$, $(CH_2)_tOH$, $(CH_2)_tOPO(OH)_2$, $(CH_2)_t$—CH=CH—$(CH_2)_vCH_3$, $(CH_2)_t$—O—$R^5$,

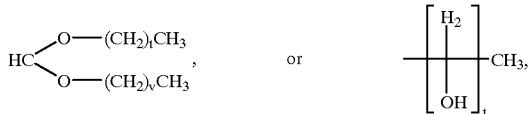

wherein t an v are, independently of one another, an integer of 0 to 14; $R^5$ is any of the above definitions of $R^1$ to $R^4$, Y is H, OH, $O(CH_2)_wCH_3$, a halogen atom,

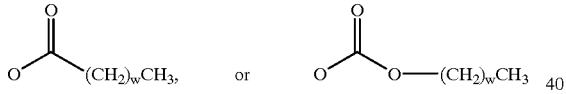

wherein w is an integer of 0 to 14.

19. The process according to claim 15, wherein the lipid A analog or a pharmacologically acceptable salt thereof is a compound represented by the following formula (II) or a pharmacologically acceptable salt thereof:

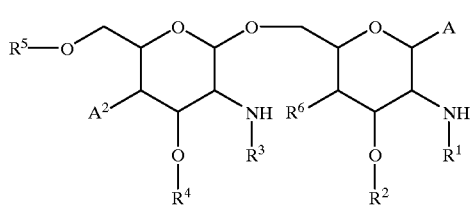

(II)

wherein $R^1$ is a group selected from the groups consisting of

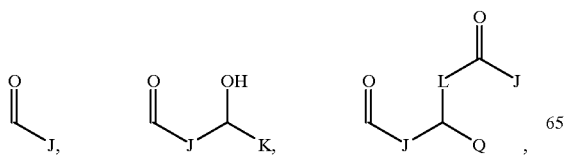

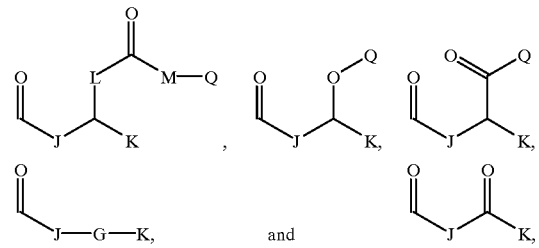

wherein J, K and Q are each a linear or branched alkyl group of 1 to 15 carbon atoms; L is O, $NH_2$ or $CH_2$; M is O or NH; G is NH, O, S, SO or $SO_2$, $R^2$ is a linear or branched alkyl group of 5 to 15 carbon atoms, $R^3$ is a group selected from the group consisting of

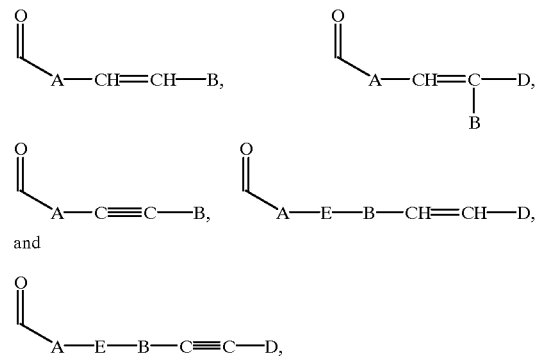

wherein E is N, O, S, SO or $SO_2$; A, B and D are each a linear or branched alkyl group of 1 to 15 carbon atoms, $R^4$ is a group selected from groups consisting of a linear or branched alkyl group of 4 to 20 carbon atoms and

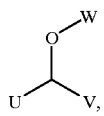

wherein U and V are each a linear or branched alkyl group of 2 to 15 carbon atoms; W is a hydrogen atom or a linear or branched alkyl group of 1 to 5 carbon atoms, $R^5$ is a group selected from the groups consisting of a hydrogen atom, J', —J'—OH, —J'—O—K', —J'—O—K'—OH and —J'—O—PO(OH)$_2$, wherein J' and K' are each a linear or branched alkyl group of 1 to 5 carbon atoms, $R^6$ is a group selected from the groups consisting of a hydroxyl group, a halogen atom, an alkoxy group of 1 to 5 carbon atoms, and a acyloxy group of 1 to 5 carbon atoms, $A^1$ and $A^2$ independently are each a group selected from the group consisting of

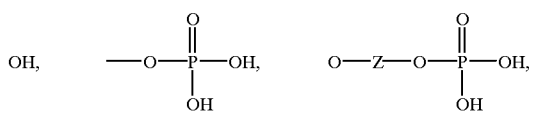

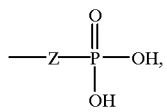 and 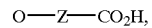

wherein Z is a linear or branched alkyl group of 1 to 10 carbon atoms.

20. The process according to claim 15, wherein the buffer has a pH of 4 to 9 and contains a saccharide.

21. The process according to claim 15, wherein the lipid analog A compound is represented by the formula (III):

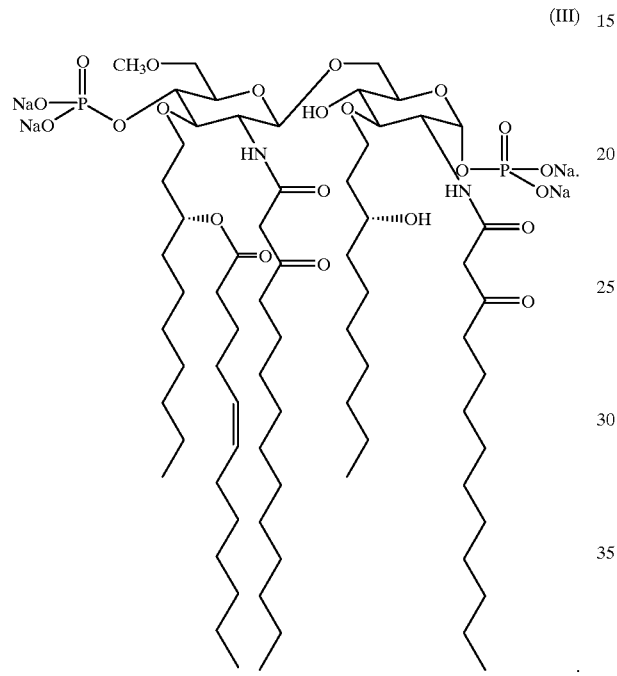

22. The process according to claim 15, wherein the lipid analog A compound is represented by the formula (IV):

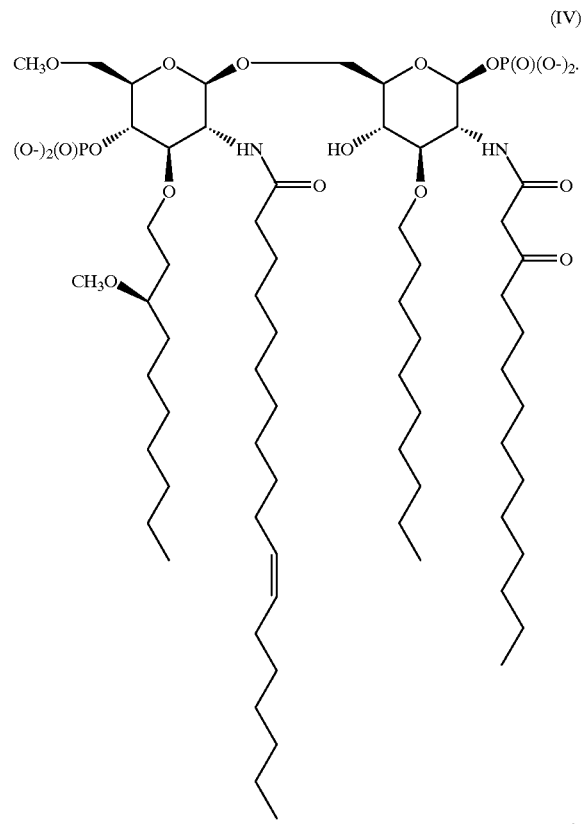

23. The process according to claim 15 produces a preparation for injection that contains aggregates having an average particle diameter of 30 nm or smaller.

24. The preparation according to claim 23, wherein the concentration of base in the alkaline aqueous solution is in the range of 0.0001M to 0.1M.

* * * * *

UNITED STATES PATENT AND TRADEMARK OFFICE
CERTIFICATE OF CORRECTION

PATENT NO.    : 6,235,724 B1
DATED         : May 22, 2001
INVENTOR(S)   : Yasuyuki Asai et al.

It is certified that error appears in the above-identified patent and that said Letters Patent is hereby corrected as shown below:

<u>Title page,</u>
Item [30], Foreign Application Priority Data, please change the priority date from "Jul. 31, 1996" to -- Jul. 3, 1996 --.

Signed and Sealed this

Twenty-sixth Day of February, 2002

Attest:

JAMES E. ROGAN
*Attesting Officer*   *Director of the United States Patent and Trademark Office*